(12) United States Patent
Nakamura et al.

(10) Patent No.: US 11,125,892 B2
(45) Date of Patent: Sep. 21, 2021

(54) RADIATION DETECTION SYSTEM, RADIATION OUTPUT DEVICE, AND RADIATION DETECTION DEVICE

(71) Applicant: FUJIFILM Corporation, Tokyo (JP)

(72) Inventors: Kenji Nakamura, Kanagawa (JP); Kouichi Kitano, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 16/551,684

(22) Filed: Aug. 26, 2019

(65) Prior Publication Data

US 2019/0383951 A1    Dec. 19, 2019

Related U.S. Application Data

(63) Continuation of application No. PCT/JP2018/006573, filed on Feb. 22, 2018.

(30) Foreign Application Priority Data

Feb. 28, 2017    (JP) .............................. JP2017-036363

(51) Int. Cl.
*G01T 1/15* (2006.01)
*G01T 1/16* (2006.01)
(Continued)

(52) U.S. Cl.
CPC .................. *G01T 1/16* (2013.01); *G01T 1/15* (2013.01); *G01T 7/02* (2013.01); *H04N 5/32* (2013.01); *A61B 6/4405* (2013.01)

(58) Field of Classification Search
CPC ....... A61B 6/4405; G01T 7/00; G01T 1/1603; G01T 1/16; G01T 1/15; G01T 1/02; H04N 5/32
See application file for complete search history.

(56) References Cited

U.S. PATENT DOCUMENTS 9,146,326 B2 * 9/2015 Kuwabara ............. G01T 1/2018
9,445,030 B2    9/2016 Yagi et al.
(Continued)

FOREIGN PATENT DOCUMENTS

JP    2008228914    10/2008
JP    2011212428    10/2011
(Continued)

OTHER PUBLICATIONS

"International Search Report (Form PCT/ISA/210) of PCT/JP2018/006573," dated May 29, 2018, with English translation thereof, pp. 1-4.
(Continued)

*Primary Examiner* — David P Porta
*Assistant Examiner* — Fani Boosalis
(74) *Attorney, Agent, or Firm* — JCIPRNET (57) ABSTRACT

The present disclosure provides a radiation detection system, a radiation output device, and a radiation detection device. The radiation detection system includes a radiation output device having an output control unit, and a radiation detection device having a recognition unit that recognizes whether radiation has been output from the radiation output device on the basis of a radiation detection signal. The output control unit causes radiation to be output at a first intensity from a time point of the start of outputting of radiation, and then causes the radiation to be output at a second intensity. The first intensity is an intensity higher than the second intensity and satisfying a threshold value condition set in advance in the recognition unit. The recognition unit recognizes that a detection signal of the radiation with the first intensity satisfies the threshold value condition, thereby recognizing the start of outputting of the radiation.

7 Claims, 4 Drawing Sheets

(51) Int. Cl.
*G01T 7/02* (2006.01)
*H04N 5/32* (2006.01)
*A61B 6/00* (2006.01)

(56) References Cited

U.S. PATENT DOCUMENTS

| | | |
|---|---|---|
| 10,288,747 B2 | 5/2019 | Tamura et al. |
| 10,585,196 B2 | 3/2020 | Tamura et al. |
| 2011/0228904 A1 | 9/2011 | Iwakiri et al. |
| 2013/0341525 A1 | 12/2013 | Maruta et al. |
| 2014/0119509 A1 | 5/2014 | Kaneko et al. |
| 2014/0254760 A1 | 9/2014 | Hiroike et al. |
| 2015/0378030 A1* | 12/2015 | Tamura .............. H04N 5/32 378/98.2 |
| 2018/0000442 A1 | 1/2018 | Hiroike et al. |

FOREIGN PATENT DOCUMENTS

| | | |
|---|---|---|
| JP | 2014003559 | 1/2014 |
| JP | 2014087513 | 5/2014 |
| JP | 2014171522 | 9/2014 |
| JP | 2016013149 | 1/2016 |
| JP | 2016025465 | 2/2016 |
| JP | 2016152970 | 8/2016 |

OTHER PUBLICATIONS

"Written Opinion of the International Searching Authority (Form PCT/ISA/237) of PCT/JP2018/006573," dated May 29, 2018, with English translation thereof, pp. 1-9.

Office Action of Japan Counterpart Application, with English translation thereof, dated Apr. 7, 2020, pp. 1-6.

* cited by examiner

| PATIENT INFORMATION | FIRST INTENSITY |
|---|---|
| PATIENT 1 | X1_5 |
| PATIENT 2 | X1_6 |
| PATIENT 3 | X1_7 |
| PATIENT 4 | X1_8 |
| ⋮ | ⋮ |

# RADIATION DETECTION SYSTEM, RADIATION OUTPUT DEVICE, AND RADIATION DETECTION DEVICE

CROSS-REFERENCE TO RELATED APPLICATION

The present application is a Continuation of PCT International Application No. PCT/JP2018/006573 filed on Feb. 22, 2018, which claims priority under 35 U.S.C. § 119(a) to Japanese Patent Application No. 2017-036363 filed on Feb. 28, 2017. Each of the above applications is hereby expressly incorporated by reference, in its entirety, into the present application.

BACKGROUND

Technical Field

The present disclosure relates to a radiation detection system that outputs radiation to a photographic subject and detects radiation transmitted through the photographic subject, and a radiation output device and a radiation detection device in the radiation detection system.

Description of the Related Art

A radiation detection system constituted by a radiation output device including an X-ray tube and so on, and a radiation detection device including a radiographic image detector such as an FPD (Flat Panel Detector) that detects radiation output from the radiation output device and transmitted through a patient has been proposed in the related art (see, for example, JP2016-25465A).

In the radiation detection system, when no radiation is emitted, the radiographic image detector undergoes preparation operation control so as to periodically reset an electric charge signal accumulated by leakage current. When the emission of radiation is started, a transition occurs from the preparation operation control to electric charge accumulation control. In the electric charge accumulation control, an electric charge signal corresponding to a dose of radiation transmitted through the patient is accumulated in each pixel of the radiographic image detector.

To allow the radiographic image detector to transition from the preparation operation control to the electric charge accumulation control in response to the start of emission of radiation, it is necessary to provide synchronization between the radiation output device and the radiation detection device.

Examples of the method for providing synchronization between the radiation output device and the radiation detection device include a method for exchanging a signal for permitting the start of outputting of radiation or a signal indicating that radiation is being output between the radiation output device and the radiation detection device by using wired or wireless connection.

Other examples include a method for recognizing the start of outputting of radiation on the basis of a signal output from the radiographic image detector.

SUMMARY

The latter method among the methods for providing synchronization described above has a problem in that if radiation output from the radiation output device has a low intensity, the radiation is difficult to discriminate from noise when detected by the radiographic image detector, and the start of outputting of the radiation is not recognizable or it takes time until the start of outputting of the radiation is recognized.

In particular, a portable radiation output device and radiation detection device used in a patient's room in the hospital, the patient's home, and the like have been proposed in recent years. To suppress the amount of radiation exposure in the surroundings, it is preferable that the dose of radiation output from the radiation output device be low, and the problem described above is likely to occur in the portable radiation output device described above.

To address the problem described above, it is an object of the present disclosure to provide a radiation detection system in which a radiation detection device is capable of accurately detecting the start of outputting of radiation from a radiation output device, the radiation output device, and the radiation detection device.

A radiation detection system according to an aspect of the present disclosure includes a radiation output device having a radiation generation unit that generates radiation, and an output control unit that controls output of the radiation, and a radiation detection device having a detection unit that detects the radiation output from the radiation output device and outputs a radiation detection signal, and a recognition unit that recognizes whether radiation has been output from the radiation output device on the basis of the radiation detection signal output from the detection unit. The output control unit of the radiation output device causes the radiation to be output at a first intensity from a time point of a start of outputting of the radiation, and then causes the radiation to be output at a second intensity. The first intensity is an intensity higher than the second intensity and satisfying a threshold value condition set in advance in the recognition unit of the radiation detection device. The recognition unit of the radiation detection device recognizes that a detection signal of the radiation with the first intensity satisfies the threshold value condition, thereby recognizing that radiation has been output from the radiation output device.

In the radiation detection system according to an aspect of the present disclosure, furthermore, the output control unit can change the first intensity for each imaging site or patient to be irradiated with the radiation output from the radiation output device.

In the radiation detection system according to an aspect of the present disclosure, furthermore, the radiation detection device can include a radiographic image detector that detects radiation output from the radiation output device and transmitted through a photographic subject, and the radiographic image detector can start accumulation of a detection signal of the radiation transmitted through the photographic subject on the basis of a time point when an output of radiation is recognized by the recognition unit.

In the radiation detection system according to an aspect of the present disclosure, furthermore, the detection unit of the radiation detection device can be at least a portion of the radiographic image detector.

A radiation output device according to an aspect of the present disclosure is a radiation output device including a radiation generation unit that generates radiation, and an output control unit that controls output of the radiation. The output control unit causes the radiation to be output at a first intensity from a time point of a start of outputting of the radiation, and then causes the radiation to be output at a second intensity. The first intensity is an intensity higher than the second intensity and satisfying a threshold value condition set in advance in the radiation detection device to allow a radiation detection device that detects the radiation to recognize a start of outputting of the radiation.

In the radiation output device according to an aspect of the present disclosure, furthermore, the output control unit can change the first intensity for each imaging site or patient to be irradiated with the radiation output from the radiation output device.

A radiation detection device according to an aspect of the present disclosure includes a radiographic image detector that detects radiation output from a radiation output device that outputs the radiation at a first intensity and then outputs the radiation at a second intensity lower than the first intensity, a detection control unit that controls the radiographic image detector, and a recognition unit that recognizes whether radiation has been output from the radiation output device. The recognition unit recognizes that a detection signal of the radiation with the first intensity output from the radiation output device satisfies a preset threshold value condition, the detection signal being input to the recognition unit within a preset detection period, thereby recognizing that radiation has been output from the radiation output device. The detection control unit controls the radiographic image detector on the basis of a time point when an output of radiation is recognized by the recognition unit to start accumulation of an electric charge signal generated by irradiation with radiation transmitted through a photographic subject.

In the radiation detection device according to an aspect of the present disclosure, furthermore, the recognition unit can recognize that the preset threshold value condition is satisfied on the basis of a radiation detection signal output from the radiographic image detector.

According to a radiation detection system, a radiation output device, and a radiation detection device according to an aspect of the present disclosure, the radiation output device outputs radiation with a first intensity higher than a second intensity from the time point of the start of outputting of the radiation, and the radiation detection device recognizes whether a radiation detection signal corresponding to the radiation with the first intensity satisfies a preset threshold value condition, thereby recognizing that radiation has been output from the radiation output device. This enables the radiation detection device to easily discriminate a radiation detection signal obtained by detecting the radiation output from the radiation output device from noise and to accurately detect the start of outputting of radiation from the radiation output device.

BRIEF DESCRIPTION OF THE DRAWINGS

Exemplary embodiments of the present invention will be described in detail based on the following figures, wherein.

DETAILED DESCRIPTION

Figure 1:
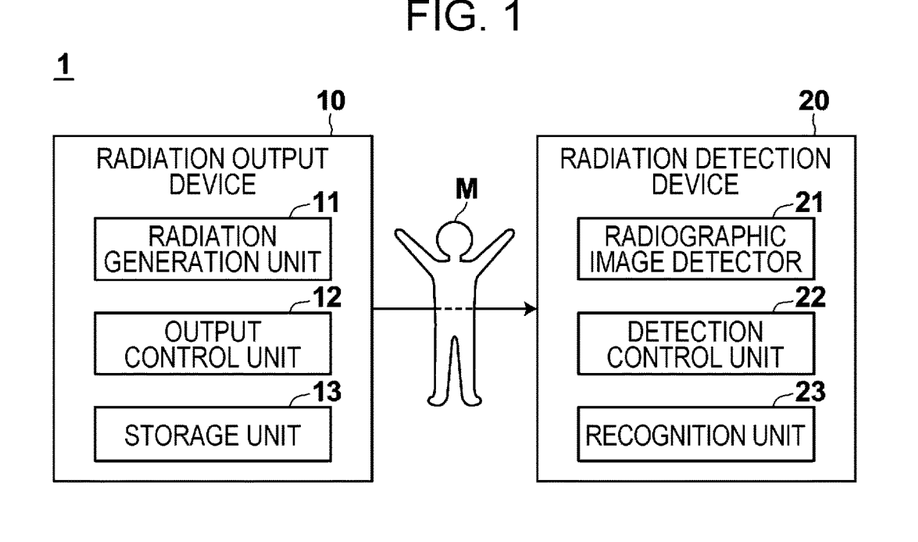
FIG. 1 is a block diagram illustrating a schematic configuration of a radiation detection system according to an embodiment of the present disclosure.

The following describes a radiation detection system, a radiation output device, and a radiation detection device according to an embodiment of the present disclosure in detail with reference to the drawings. FIG. 1 is a block diagram illustrating a schematic configuration of the radiation detection system of this embodiment.

As illustrated in FIG. 1, a radiation detection system 1 of this embodiment includes a radiation output device 10 and a radiation detection device 20. The radiation output device 10 is preferably portable, and the radiation detection device 20 is also preferably a portable cassette. However, the present disclosure is not limited to a portable radiation detection system, and is also applicable to mountable radiation detection systems such as a radiation detection system that captures an image of a photographic subject in standing position and a radiation detection system that captures an image of a photographic subject in lying position.

The radiation output device 10 outputs radiation to a photographic subject M such as a patient. The radiation output device 10 includes a radiation generation unit 11 that generates radiation, an output control unit 12 that controls output of the radiation, and a storage unit 13.

The radiation generation unit 11 includes a radiation source such as an X-ray tube. The radiation generation unit 11 generates radiation due to the application of a high voltage.

The output control unit 12 includes, for example, a CPU (Central Processing Unit) and so on. The output control unit 12 controls output of radiation from the radiation output device 10. Specifically, the output control unit 12 controls a tube voltage and tube current to be applied to the radiation generation unit 11, such that the output control unit 12 controls the tube voltage or tube current to control the intensity of radiation to be emitted from the radiation generation unit 11 and the duration of emission.

To allow the radiation detection device 20 to recognize that the radiation output device 10 has started outputting radiation, the output control unit 12 controls the radiation generation unit 11 to output radiation at a first intensity from the time point of the start of outputting of the radiation and then output radiation at a second intensity.

Figure 2:
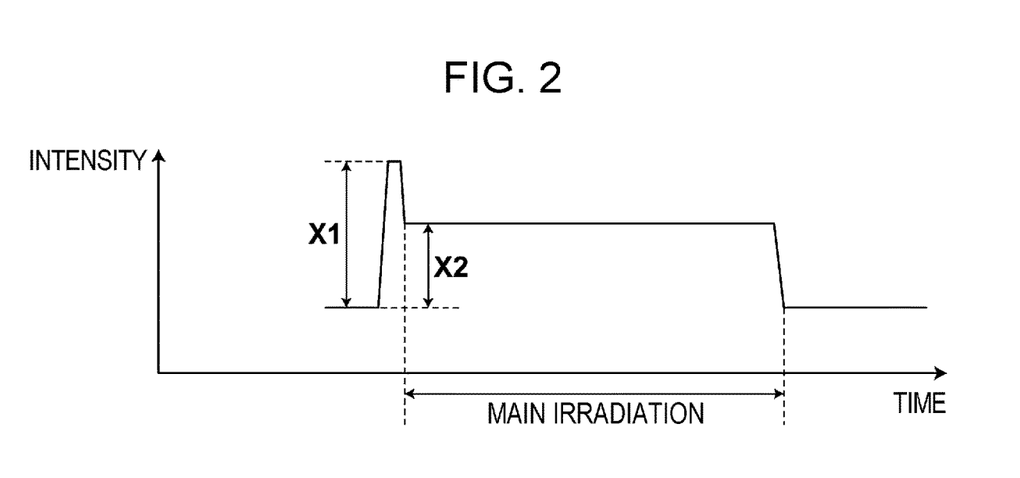
FIG. 2 is a diagram illustrating an example of radiation output from a radiation output device according to an embodiment of the present disclosure.

For example, as illustrated in FIG. 2, the output control unit 12 of this embodiment outputs radiation having a first intensity X1 and then output radiation having a second intensity X2. The first intensity X1 is set higher than the second intensity X2. The first intensity X1 is set to an intensity satisfying a threshold value condition set in advance in a recognition unit 23 of the radiation detection device 20 described below. The intensity satisfying the threshold value condition will be described in detail below.

As a specific example of the first intensity X1 and the second intensity X2, for example, radiation with the first intensity X1 may be output for a period of 1 ms, with the tube voltage and the tube current of the radiation generation unit 11 set to 70 kV and 10 mA, respectively, and then radiation with the second intensity X2 may be output, with the tube voltage kept at 70 kV and the tube current set to 2 mA.

The first intensity X1, the output period of the first intensity X1, and the second intensity X2 are not limited to those in the example described above. Further, in terms of deterioration of the radiation generation unit 11, the output period of radiation with the first intensity X1 is preferably 10 µs to 1 ms.

The first intensity X1 may be made changeable by the output control unit 12 accepting a change of the first intensity X1. For example, the first intensity X1 may be changed for each hospital, clinical department, or technician.

The storage unit 13 stores information on the first intensity X1, the output period of the first intensity X1, and the second intensity X2 of the radiation described above. The storage unit 13 is constituted by a semiconductor memory, a register, or the like. The output control unit 12 controls the radiation generation unit 11 on the basis of the information stored in the storage unit 13 to output radiation with the first intensity X1 and the second intensity X2.

The radiation detection device 20 includes a radiographic image detector 21, a detection control unit 22, and the recognition unit 23.

The radiographic image detector 21 detects radiation output from the radiation output device 10 and transmitted through the photographic subject M and outputs a radiation detection signal. Examples of the radiographic image detector 21 include a device including a scintillator (fluorescent body) that converts incident radiation into visible light and a TFT (Thin Film Transistor) active matrix substrate. The radiographic image detector 21 is not limited to this, and may be a so-called direct-conversion radiographic image detector that converts incident radiation directly into an electric charge signal. In this embodiment, the radiographic image detector 21 corresponds to a detection unit according to an aspect of the present disclosure.

Figure 3:
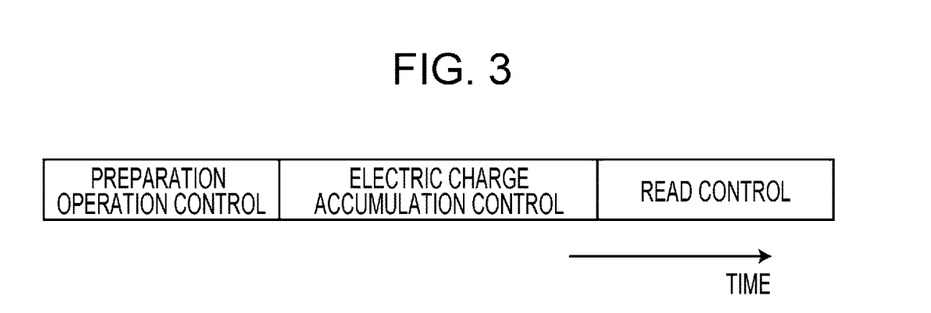
FIG. 3 is a diagram for describing operation control for a radiographic image detector.

The detection control unit 22 includes, for example, a CPU and so on. The detection control unit 22 controls the operation of the radiographic image detector 21. The operation control for the radiographic image detector 21 includes preparation operation control, electric charge accumulation control, and read control, as illustrated in FIG. 3.

During the period of the preparation operation control for the radiographic image detector 21, a high voltage is applied to the radiographic image detector 21 to allow the radiographic image detector 21 to detect radiation. During the period of the preparation operation control, a radiation detection signal is read from the radiographic image detector 21 in a preset detection period (corresponding to a detection period according to an aspect of the present disclosure), and is output to the recognition unit 23.

As the radiation detection signal output from the radiographic image detector 21 to the recognition unit 23 during the period of the preparation operation control, a signal output from one preset pixel (detection element) in the radiographic image detector 21 may be used, or the sum, mean, median, or the like of signals output from some pixels or the sum, mean, median, or the like of signals output from all the pixels may be used.

The recognition unit 23 recognizes that the radiation detection signal input during the period of the detection period described above satisfies a preset threshold value condition, thereby recognizing that radiation has been output from the radiation output device 10. Examples of the threshold value condition include whether a radiation detection signal input at any time point has a magnitude greater than or equal to a preset threshold value, and whether a time-integrated value of radiation detection signals over a preset period (for example, one detection period) is greater than or equal to a preset threshold value. The first intensity X1 of the radiation described above and the output period of the first intensity X1 are set so that such a threshold value condition is satisfied.

When the recognition unit 23 recognizes that radiation has been output from the radiation output device 10, a recognition signal is output from the recognition unit 23 to the detection control unit 22. The detection control unit 22 starts the electric charge accumulation control at the time point when the recognition signal is input. Specifically, the detection control unit 22 controls the radiographic image detector 21 to start accumulation of electric charge generated by irradiation with radiation transmitted through the photographic subject M. The accumulation of electric charge is performed for a preset main irradiation period.

Then, the detection control unit 22 starts the read control from the time when the main irradiation period ends. Specifically, the detection control unit 22 controls the radiographic image detector 21 to start reading an electric charge signal accumulated during the main irradiation period. A radiation detection signal corresponding to the electric charge signal read from the radiographic image detector 21 is stored in a storage medium such as a memory disposed in the radiation detection device 20. The radiation detection signal stored in the storage medium is subjected to predetermined signal processing and is then output to a device such as a console.

Figure 4:
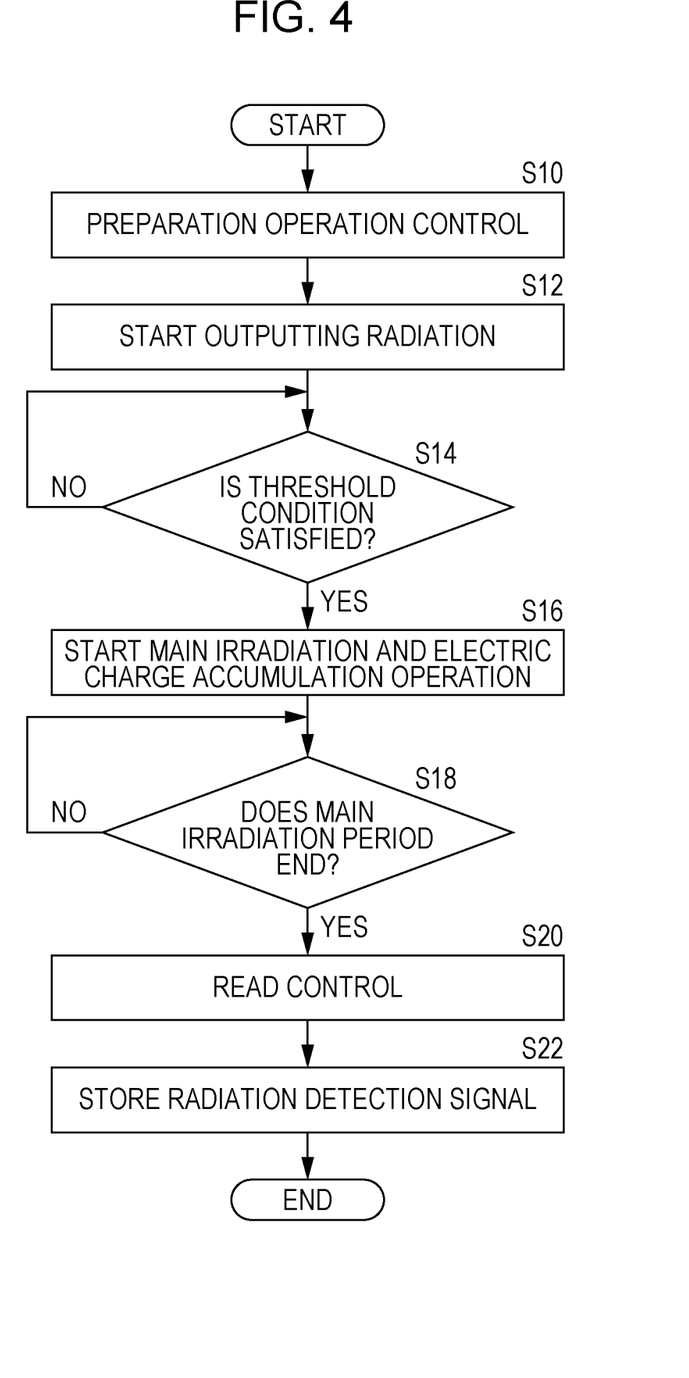
FIG. 4 is a flowchart for describing the operation of the radiation detection system according to an embodiment of the present disclosure.

Next, the operation of the radiation detection system of this embodiment will be described with reference to a flowchart illustrated in FIG. 4.

First, in the radiation detection device 20, the detection control unit 22 performs control to start the preparation operation of the radiographic image detector 21 (S10).

After the photographic subject M is placed at a predetermined position of the radiographic image detector 21, a technician or the like inputs a radiation exposure instruction, and the radiation output device 10 starts outputting radiation in accordance with the radiation exposure instruction (S12).

The radiation output device 10 outputs radiation with the first intensity X1 described above from the time point of the start of outputting of the radiation, and the radiation with the first intensity X1 is detected by the radiographic image detector 21 of the radiation detection device 20. A radiation detection signal output from the radiographic image detector 21 is input to the recognition unit 23, and the recognition unit 23 recognizes whether the radiation detection signal corresponding to the radiation with the first intensity X1 satisfies a preset threshold value condition. If it is recognized that the preset threshold value condition is satisfied (S14, YES), the recognition unit 23 outputs a recognition signal to the detection control unit 22.

After outputting the radiation with the first intensity X1 described above, the radiation output device 10 outputs radiation with the second intensity X2 to start main irradiation. On the other hand, the detection control unit 22 of the radiation detection device 20 controls the radiographic image detector 21 to start an electric charge accumulation operation from the time point when the recognition signal is input (S16).

Then, at the time point when the radiation is output for the preset main irradiation period (S18, YES), the radiation output device 10 stops outputting the radiation. On the other hand, the detection control unit 22 of the radiation detection device 20 starts the reading operation of the radiographic image detector 21 (S20).

Then, the radiation detection signal output from the radiographic image detector 21 is stored in the storage medium such as a memory (S22).

According to the radiation detection system 1 of the embodiment described above, the radiation output device 10 outputs radiation with the first intensity X1 higher than the second intensity X2 from the time point of the start of outputting of the radiation, and the radiation detection device 20 recognizes whether the radiation detection signal corresponding to the radiation with the first intensity X1 satisfies a preset threshold value condition, thereby recognizing that radiation has been output from the radiation output device 10. Thus, a radiation detection signal obtained by detecting the radiation output from the radiation output device 10 can be easily discriminated from noise, and the start of outputting of radiation from the radiation output device 10 can be accurately detected.

Figure 5:
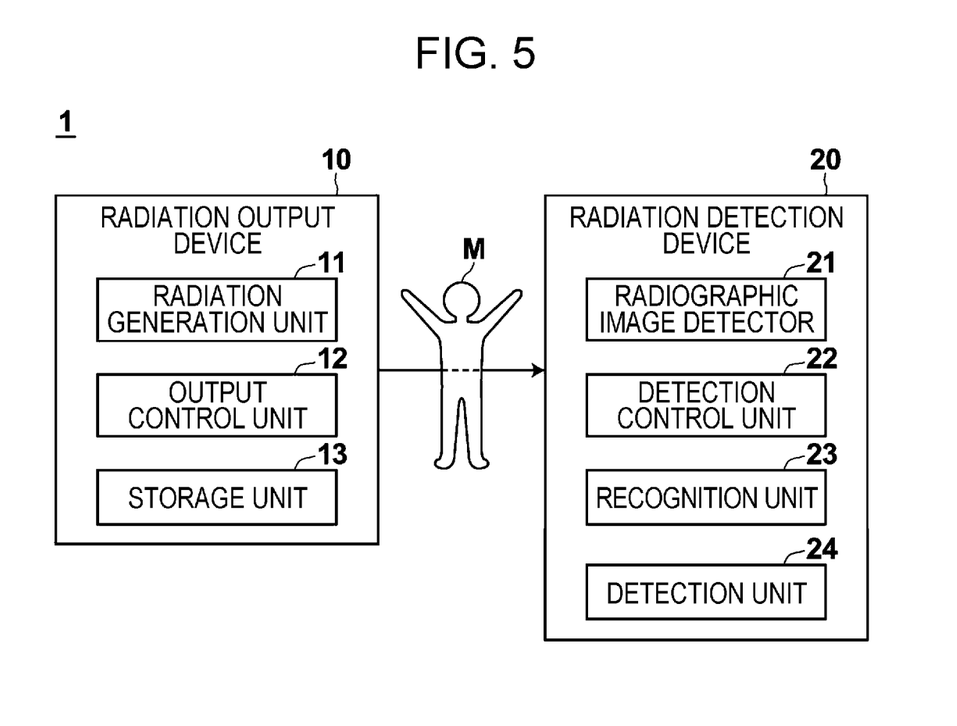
FIG. 5 is a block diagram illustrating a schematic configuration of another embodiment of the radiation detection system according to an aspect of the present disclosure.

In the radiation detection system 1 of the embodiment described above, the recognition unit 23 recognizes output of radiation by using a radiation detection signal output from the radiographic image detector 21. However, this is not limiting, and, as illustrated in FIG. 5, a detection unit 24 that detects radiation output from the radiation output device 10 may be disposed separately from the radiographic image detector 21. The recognition unit 23 may recognize output of radiation by using a radiation detection signal output from the detection unit 24.

Figure 6:
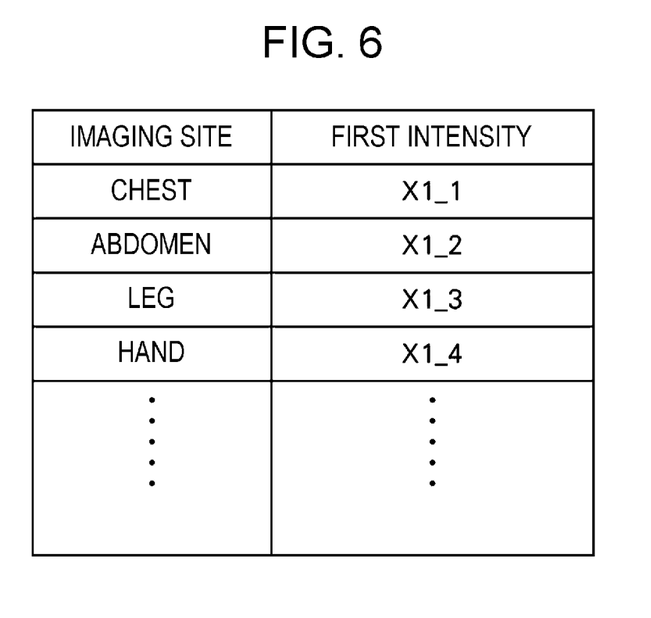
FIG. 6 is a diagram illustrating a table in which imaging sites and first intensities at the start of outputting of radiation are associated with each other.
Figure 7:
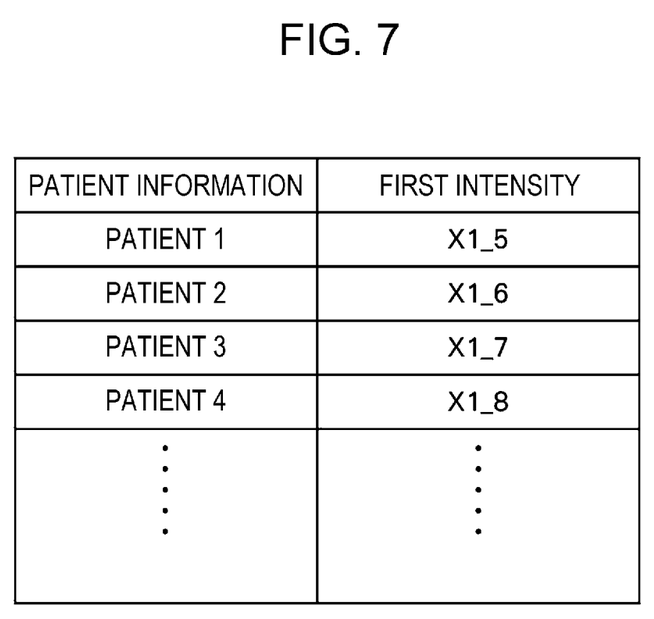
FIG. 7 is a diagram illustrating a table in which patient information and first intensities at the start of outputting of radiation are associated with each other.

In addition, the first intensity X1 of the radiation described above may be changed for each imaging site or patient that is irradiated with the radiation. Specifically, as illustrated in FIG. 6, a table in which imaging sites and first intensities are associated with each other may be disposed, or, as illustrated in FIG. 7, a table in which patient information and first intensities are associated with each other may be disposed. These tables may be referenced to change the first intensity X1. In this way, changing the first intensity X1 can prevent an unnecessary increase in the amount of radiation exposure to the patient.

The disclosure of JP2017-036363 is incorporated herein by reference in its entirety.

All the documents, patent applications, and technical standards mentioned in this specification are incorporated herein by reference to the same extent as if each individual document, patent application, and technical standard were specifically and individually indicated to be incorporated by reference.

What is claimed is:

1. A radiation detection system comprising:
   a radiation output device having an X-ray tube that generates radiation, and a processor that controls output of the radiation; and
   a radiation detection device having a radiographic image detector that detects the radiation output from the radiation output device and outputs a radiation detection signal, and a recognition circuit that recognizes whether radiation has been output from the radiation output device on the basis of the radiation detection signal output from the radiographic image detector, wherein
   the processor of the radiation output device causes the radiation to be output at a first intensity from a time point of a start of outputting of the radiation to a start of a main irradiation period, and then causes the radiation to be output at a second intensity during the main irradiation period,
   the first intensity is an intensity higher than the second intensity and satisfying a threshold value condition set in advance in the recognition circuit of the radiation detection device, and
   the recognition circuit of the radiation detection device recognizes that a detection signal of the radiation with the first intensity satisfies the threshold value condition, thereby recognizing that radiation has been output from the radiation output device,
   wherein the radiation detection device comprises a radiographic image detector that detects radiation output from the radiation output device and transmitted through a photographic subject, and the radiographic image detector performs accumulation of a detection signal of the radiation transmitted through the photographic subject during the main irradiation period.

2. The radiation detection system according to claim 1, wherein
   the processor changes the first intensity for each imaging site or patient to be irradiated with the radiation output from the radiation output device.

3. The radiation detection system according to claim 1, wherein
   the radiographic image detector of the radiation detection device is at least a portion of the radiographic image detector.

4. A radiation output device comprising an X-ray tube that generates radiation, and a processor that controls output of the radiation, wherein
   the processor causes the radiation to be output at a first intensity from a time point of a start of outputting of the radiation to a start of a main irradiation period, and then causes the radiation to be output at a second intensity during the main irradiation period, and
   the first intensity is an intensity higher than the second intensity and satisfying a threshold value condition set in advance in a radiation detection device to allow a radiation detection device that detects the radiation to recognize a start of outputting of the radiation,
   wherein the radiation detection device comprises a radiographic image detector that detects radiation output from the radiation output device and transmitted through a photographic subject, and the radiographic image detector performs accumulation of a detection signal of the radiation transmitted through the photographic subject during the main irradiation period.

5. The radiation output device according to claim 4, wherein
   the processor changes the first intensity for each imaging site or patient to be irradiated with the radiation output from the radiation output device.

6. A radiation detection device comprising:
   a radiographic image detector that detects radiation output from a radiation output device that outputs the radiation at a first intensity from a time point of a start of outputting of the radiation to a start of a main irradiation period, and then outputs the radiation at a second intensity lower than the first intensity during a main irradiation period;
   a processor that controls the radiographic image detector; and
   a recognition circuit that recognizes whether radiation has been output from the radiation output device, wherein the recognition circuit recognizes that a detection signal of the radiation with the first intensity output from the radiation output device satisfies a preset threshold value condition, the detection signal being input to the recognition circuit within a preset detection period, thereby recognizing that radiation has been output from the radiation output device, and the processor controls the radiographic image detector on the basis of a time point when an output of radiation is recognized by the recognition circuit to start accumulation of an electric charge signal generated by irradiation with radiation transmitted through a photographic subject during the main irradiation period.

7. The radiation detection device according to claim 6, wherein the recognition circuit recognizes that the preset threshold value condition is satisfied on the basis of a radiation detection signal output from the radiographic image detector.

* * * * *